(12) United States Patent
Yuasa et al.

(10) Patent No.: US 6,255,444 B1
(45) Date of Patent: Jul. 3, 2001

(54) AROMATIC ESTER (METH)ACRYLATE DENDRIMERS AND CURABLE RESIN COMPOSITION

(75) Inventors: Masatoshi Yuasa, Yokohama; Hironobu Kawasato, Kisarazu; Takero Teramoto, Hiratsuka, all of (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/485,849

(22) PCT Filed: Aug. 7, 1998

(86) PCT No.: PCT/JP98/03648

§ 371 Date: Feb. 17, 2000

§ 102(e) Date: Feb. 17, 2000

(87) PCT Pub. No.: WO99/08993

PCT Pub. Date: Feb. 25, 1999

(30) Foreign Application Priority Data

Aug. 18, 1997 (JP) .................................... 9-221491

(51) Int. Cl.[7] .......................... C08G 63/00; C08G 63/16; C08G 63/18; C08F 299/04
(52) U.S. Cl. .................. 528/308.6; 528/308; 525/44; 525/61; 525/309; 525/327.7; 525/330.1
(58) Field of Search ................ 525/309, 327.7, 525/330.1, 61, 44; 528/308.6, 308

(56) References Cited

U.S. PATENT DOCUMENTS 5,225,522 * 7/1993 Turner et al. ................ 528/327

FOREIGN PATENT DOCUMENTS

| 5-214045 | 8/1996 | (JP) . |
| 8-214045 | 10/1996 | (JP) . |
| 8-283357 | 10/1996 | (JP) . |

OTHER PUBLICATIONS

Patent Abstracts of Japan, Publication No. 05214045 (Aug. 24, 1993).
Patent Abstracts of Japan, Publication No. 08283357 (Oct. 29, 1996).

* cited by examiner

*Primary Examiner*—James J. Seidleck
*Assistant Examiner*—Olga Asinovsky
(74) *Attorney, Agent, or Firm*—Birch, Stewart, Kolasch & Birch, LLP (57) ABSTRACT

This invention relates to an aromatic ester (meth)acrylate dendrimer composed of the core formed by an aromatic polycarboxylic acid and the branches formed by an aromatic compound containing one hydroxyl group and two carboxyl groups and represented by the following general formula (1)

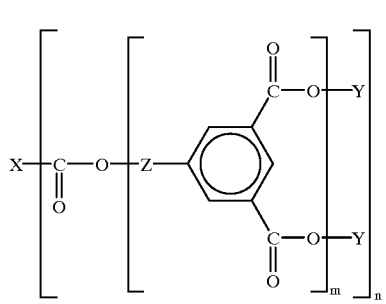

(1)

and also to a curable resin composition which contains the dendrimer and a polymerization initiator as essential components, is low in viscosity and highly curable, and forms a coating film with excellent heat and moisture resistance.

4 Claims, 2 Drawing Sheets

AROMATIC ESTER (METH)ACRYLATE DENDRIMERS AND CURABLE RESIN COMPOSITION

This application is the national phase under 35 U.S.C. §371 of PCT International Application No. PCT/JP98/03648 which has an International filing date of Aug. 17, 1998, which designated the United States of America.

FIELD OF TECHNOLOGY

This invention relates to aromatic ester (meth)acrylate dendrimers of highly branched structure and curable resin compositions containing said dendrimers as essential component.

BACKGROUND TECHNOLOGY

Curable resin compositions are generally used in coatings, adhesives, and molding materials because of their thermal and mechanical properties. These curable resins are mainly composed of oligomers and monomers and their concrete examples are epoxy acrylates, urethane acrylates, ester acrylates, and unsaturated polyesters. Of these compounds, particularly the oligomeric components exert a great influence on the properties of the coating films to be formed after curing or those of the molded articles and, in consequence, the properties of the oligomeric components assume great importance for manifestation of good material performance. These compounds generally have a linear molecular structure and tend to increase in voscosity and become highly viscous as their molecular weight and content increase; thus it becomes necessary to use the monomeric component and, in some cases, an organic solvent in order to adjust the viscosity to an optimal level for usage.

The monomers used in this manner, however, have a low density of functional groups per molecule and lower the crosslinking density after curing and, furthermore, the residual monomers remaining unreacted in the coating film after curing degrade the mechanical and thermal properties of the film.

In addition, the use of monomeric components and organic solvents is a disadvantage during work on account of odor and, in particular, the use of organic solvents is not necessarily a desirable method for controlling the viscosity because of a growing tendency to avoid it from the standpoint of reducing the release of volatile components.

The use of liquid polyfunctional monomers is another approach to solve the aforementioned problems, but the effect which the monomers of this type produce for lowering the viscosity is no more pronounced than that of monomeric components and organic solvents and, furthermore, the polyfunctionality tends to cause the coating film to undergo large shrinkage after curing and has made it difficult to obtain satisfactory results in respect to the properties of coated films, particularly long-term reliability at high temperature and high humidity.

The present inventors have conducted extensive studies to solve such long outstanding problems, come across aromatic ester (meth)acrylate dendrimers which have a highly branched molecular chain containing terminal (meth) acrylate groups, found that the use of such dendrimers gives curable resin compositions which form cured films of excellent heat and moisture resistance, and completed this invention.

Accordingly, an object of this invention is to solve the aforementioned problems and provide novel aromatic ester (meth)acrylate dendrimers which are low in viscosity, highly curable, and capable of forming cured films of excellent heat and moisture resistance and curable resin compositions containing said dendrimers as essential component.

DISCLOSURE OF THE INVENTION

Thus, this invention relates to an aromatic ester (meth) acrylate dendrimer represented by the following general formula (1)

(1)

(in which X is a core-forming aromatic residue of an aromatic compound of 6 to 20 carbon atoms, Y is an organic group of 6 to 20 carbon atoms containing (meth)acrylic group, Z is direct linkage or an aromatic residue of 6 to 20 carbon atoms, m is the number of repeating units from 1 to 10, and n is an integer from 3 to 6).

This invention further relates to a curable resin composition containing the aforementioned aromatic ester (meth) acrylate dendrimer and a polymerization initiator as essential components and to the film obtained by applying the curable resin composition to the substrate.

In an aromatic ester (meth)acrylate dendrimer of this invention, the core X is the aromatic residue originating from the reactant polycarboxylic acid represented by the following general formula $X(COOH)_n$ (in which X and n are as defined above) or its derivative such as acid anhydride and acid halide and it preferably comes from aromatic compounds containing the following nucleus

(in which A is a divalent group or direct linakge). Groups preferable as the linking group A are —O—, —S—, —SO$_2$—, —CO—, and direct linkage.

In these compounds, the integer n indicating the number of carboxyl groups (including the groups derived from the carboxyl group such as acid halide group and the same holds true hereinafter) in the molecule is preferably 3 to 6. Where n is 2, the molecular chain extends only in two directions with a low degree of branching and the resulting compound is not much different in structure from linear compounds and, undesirably, the special feature which constitutes the object of this invention cannot be manifested. Where n exceeds 6, branched molecular chains tend to become crowded together and, also undesirably, the degree of branching does not increase under the influence of steric hindrance.

Examples of such polycarboxylic acids are 1,3,5-benzenetricarboxylic acid, 1,2,4-benzenetricarboxylic acid, 3,3',4,4'-benzophenonetetracarboxylic acid, 3,3',4,4'-biphenyltetracarboxylic acid, 3,3',4,4'-(diphenyl ether)tetracarboxylic acid, 3,3',4,4'-(diphenyl sulfone)tetracarboxylic acid, 2,3',3',4'-benzophenonetetracarboxylic acid, 2,3',3',4'-biphenyltetracarboxylic acid, 2,3',3',4'-(diphenyl ether)tetracarboxylic acid, 2,3',3',4'-(diphenyl sulfone)tetracarboxylic acid, 2,2'-bis(3,4-dicarboxyphenoxyphenyl) sulfone, 1,4,5,8-naphthalenetetracarboxylic acid, 2,3,6,7-naphthalenetetracarboxylic acid, pyromellitic acid, mellitic acid, and their derivatives.

In an aromatic ester (meth)acrylate dendrimer of this invention, the highly branched portions are formed by the aromatic residue originating from the reactant aromatic compound containing one hydroxyl group and two carboxylic groups or groups derivative therefrom represented by the following general formula (in which Z is defined as above) and the group Z is preferably direct linkage or an aromatic residue of 6 to 20 carbon atoms such as shown below.

Examples of such aromatic compounds are 5-hydroxyisophthalic acid, 4-hydroxyisophthalic acid, 5-(4-hydroxybenzyloxy)isophthalic acid, 5-(4-hydroxybenzylsulfonyl)isophthalic acid, 5-(4-hydroxybenzyl)isophthalic acid, 4-(4-hydroxybenzyloxy)isophthalic acid, 4-(4-hydroxybenzylsulfonyl)isophthalic acid, 4-(4-hydroxybenzyl)isophthalic acid, 2-hydroxyterephthalic acid, 2-(4-hydroxybenzyloxy)terephthalic acid, 2-(4-hydroxybenzylsulfonyl)terephthalic acid, 2-(4-hydroxybenzyl)terephthalic acid and their derivatives.

In the aromatic ester (meth)acrylate dendrimers, the terminal groups are organic groups originating from reactants containing (meth)acrylic group represented by the following general formula

Y-H (in which Y is defined as above). The H atom here may be replaced with Na or glycidyl group.

These compounds are (meth)acrylic compounds containing hydroxyl groups or groups derivative therefrom necessary for the formation of ester linkage with the carboxylic groups in the aforementioned branch-forming components and the organic group Y is represented by the following general formula (CH$_2$=CR—COO)$_n$—Q—O—

(in which Q is a hydrocarbon group of 1 to 17 carbon atoms, R is hydrogen or methyl, and n is an integer from 1 to 5). In this invention, (meth)acrylic refers to acrylic or methacrylic and (meth)acrylate to acrylate or methacrylate.

Concretely, these compounds include pentaerythritol triacrylate, epichlorohydrin(ECH)-modified glycerol triacrylate, ECH-modified 1,6-hexanediol diacrylate, triglycerol diacrylate, ECH-modified ethylene glycol dimethacrylate, glycerol dimethacrylate, glycerol acrylate/methacrylate, ECH-modified propylene glycol diacrylate, ECH-modified trimethylolpropane triacrylate, butanediol monoacrylate, ECH-modified butyl acrylate, glycerol methacrylate, 2-hydroxyethyl acrylate, 2-hydroxyethyl methacrylate, caprolactone-modified 2-hydroxyethyl acrylate, caprolactone-modified 2-hydroxyethyl methacrylate, 2-hydroxypropyl acrylate, 2-hydroxypropyl methacrylate, ethylene oxide-modified phthalic acid acrylate, ethylene oxide-modified phthalic acid methacrylate, polyethylene glycol methacrylate, and polypropylene glycol methacrylate. It is allowable to use acrylic compounds containing glycidyl group in the molecule, for example, glycidyl methacrylate and glycidyl acrylate.

The aromatic ester (meth)acrylate dendrimers of this invention can be prepared by two approaches shown below (namely, a divergent approach and a convergent approach).

In accordance with the divergent approach, the aforementioned aromatic polycarboxyl acid as a core unit is converted to reactive acid chloride and esterified with the aforementioned branch-forming component or an aromatic compound containing one hydroxyl group and two carboxylic groups to prepare the first-generation aromatic ester, the aromatic ester is converted to acid chloride and esterified with the branch-forming component and this sequence was repeated to give the highly branched second- and higher-generation aromatic esters.

A catalyst can be used to activate this esterification reaction. Such catalysts include triethylamine, dimethylaniline, dimethylaminobenzylamine, and pyridine and the catalyst is preferably added in the range of 0.5 to 2.0 of equivalent ratio against the hydroxyl group in the branch-forming component.

The (meth)acrylic groups are introduced to the terminal sites of the highly branched aromatic ester obtained in this manner by converting the terminal carboxyl groups in the aromatic ester to acid chlorides and then esterifying with the aforementioned hydroxyl-containing (meth)acrylic compound to give an aromatic ester (meth)acrylate dendrimer. A catalyst similar to the above can be used to activate the esterification reaction here.

Also, the (meth)acrylic groups can be introduced by the reaction of the terminal carboxyl groups with a compound containing glycicyl group in the molecule. A basic catalyst can be added to activate the reaction of carboxylic acid with glycidyl group.

The convergent approach, another synthetic route to the preparation of aromatic ester (meth)acrylate dendrimers of this invention, uses a terminal component as starting material. The terminal component can be obtained by the esterification reaction of the aforementioned branch-forming component with a compound containing hydroxyl group in the molecule and, also, with a compound containing glycidyl group in the molecule. An aromatic compound containing terminal (meth)acrylic groups thus obtained is used as starting material and it is esterified with a branch-forming component and the resulting aromatic ester is further esterified with the branch-forming component. The esterification reaction is repeated and, lastly, esterified with an aromatic polycarobxylic acid as core component to yield an aromatic ester (meth)acrylate dendrimer.

A curable resin composition of this invention is formulated from an aromatic ester (meth)acrylate dendrimer and a polymerization initiator as essential components.

The polymerization initiator here is not specific and any known compound capable of initiating the polymerization of (meth)acrylic groups may be used. Where irradiation with UV is used for photocuring, a photo-initiator such as the following may be used:

2,2-dimethoxy-2-phenylacetophenone, acetophenone, benzophenone, xanthone, 3-methylacetophenone, 4-chlorobenzophenone, 4,4'-dimethoxybenzophenone, N,N,N',N'-tetramethyl-4,4'-diaminobenzophenone, benzoin propyl ether, benzyl dimethyl ketal, 1-(4-isopropylphenyl)-2-hydroxy-2-methylpropan-1-one, 2-hydroxy-2-methyl-1-phenylpropan-1-one, and thioxanthone-based compounds. These photo-initiators may be used singly or as a mixture of two kinds or more.

Curing by heat may also be used and a thermal initiator is used in this case; examples are ketone peroxides, peroxyketanols, hydroperoxides, dialkyl peroxides, diacyl peroxides, peroxydicarbonates, and peroxy esters.

These polymerization initiators can be formulated at a rate of 0.5 to 20 parts by weight per 100 parts by weight of an aromatic ester (meth)acrylate dendrimer of this invention. With less than 5 parts by weight of the initiator, the extent of polymerization declines markedly which makes it difficult to form good coating films. On the other hand, where the initiator is added in excess of 20 parts by weight, a large amount of the unreacted or decomposed initiator remains in the coating film.

When a curable resins composition containing an aromatic ester (meth)acrylate dendrimer of this invention and a polymerization initiator as essential components is used as coating or adhesive, it may be used together with polyfunctional acrylates of a number average molecular weight of 1,500 or less containing 3 or more (meth)acryloyl groups in the molecule for the purpose of improving the surface hardness and resin strength of the coating film. Such polyfunctional acrylates include dipentaerythritol hexa(meth)acrylate, dipentaerythritol penta(meth)acrylate, dipentaerythritol tetra(meth)acrylate, dipentaerythritol tri(meth)acrylate, pentaerythritol penta(meth)acrylate, pentaerythritol tri(meth)acrylate, and trimethylolpropane tri(meth)acrylate. Also included are the aforementioned (meth)acrylates which are modified with alkyl, caprolactone, ethylene oxide, or propylene oxide, (meth)acrylates of other aliphatic polyols, tris[(meth)acryloyloxyehtyl] isocyanurate, and caprolactone-modified tris[(meth)acryloyloxyehtyl] isocyanurate.

When the molecular weight of these polyfunctional acrylates exceeds 1,500, the flow properties of a coating film decrease too much to form a smooth film or the crosslinking density decreases to lower the surface hardness. Where less than 3 (meth)acryloyl groups are present in one molecule of these compounds, the crosslinking density decreases to lower the surface hardness and the resin strength.

These polyfunctional acrylates may be incorporated at a rate of 20 to 500 parts by weight per 100 parts by weight of an aromatic ester (meth)acrylate dendrimer of this invention. Incorporation of less than 20 parts by weight undesirably leads to lowered crosslinking density and, in turn, to lowered surface hardness. On the other hand, incorporation in excess of 500 parts by weight undesirably leads to a too high crosslinking density and develops a tendency toward formation of fragile coating films.

When a curable resin composition of this invention containing an aromatic ester (meth)acrylate dendrimer as essential component is used as coating, another acrylate may be used as reactive diluent to lower the viscosity of such coating. Examples of such acrylates are ethylene glycol di(meth)acrylate, 1,3-propylenediol (meth)acrylate, 1,4-butanediol (meth)acrylate, 1,5-pentanediol di(meth)acrylate, 1,6-hexanediol di(meth)acrylate, 2-hydroxyethyl (meth)acrylate, N-vinyl-2-pyrrolidone, tetrahydrofurfuryl (meth)acrylate, and N-vinylcaprolactam. These reactive diluents are incorporated at a rate of 0 to 100 parts by weight per 100 parts by weight of an aromatic ester (meth)acrylate dendrimers of this invention. Use in excess of 100 parts by weight leads to lowered crosslinking density and lowered surface hardness of the coating film.

Furthermore, it is possible to add a nonpolymerizable diluent to a curable resin composition of this invention for the purpose of optimizing the viscosity. Such diluents include, for example, ethyl acetate, butyl acetate, Methyl Cellosolve, Ethyl Cellosolve, Methyl Cellosolve acetate, Ethyl Cellosolve acetate, isopropyl alcohol, touene, and xylene. As the optimal viscosity of coatings varies greatly with the coating method, kind of coating, coating speed, and film thickness, the amount of diluent can be set at will. However, the majority of these nonpolymerizable diluents must evaporate in drying by heat in the course of curing. The diluents, if remaining in large quantities, often cause serious defects in the surface hardness and adhesion of the coating films.

It is possible to add components other than the aforementioned to curable resin compositions of this invention. Such components are, for example, pigments for the purpose of coloring and hiding the substrate, fillers, surfactants, dispersants, plasticizers, UV absorbers, and antioxidants.

In this invention, when a curable resin composition prepared with the use of a photo-initiator is, for example, intended for coating, it is applied to the substrate, heated at 80 to 100° C. for several minutes, and cured under irradiation with UV at several hundreds of $mj/cm^2$ with the aid of a high-pressure mercury vapor lamp. Similarly, a curable resin composition prepared with the use of a thermal initiator is applied to the substrate and cured by heating at 150 to 200° C. for 30 to 60 minutes.

The cured coating films thus obtained from curable resin compositions of this invention show high surface hardness, excellent heat and moisture resistance, and strong adhesion to the substrate. For this reason, they are extremely useful for protection membranes and insulation membranes for electronic materials and coatings for metallic materials.

PRRFERRED EMBODIMENTS OF THE INVENTION

A preferred mode of the execution of this invention will be described below with reference to the accompanying Synthetic Examples and Examples but this invention is not limited thereto.

Preparation of Aromatic Ester Acrylate Dendrimers A to L

SYNTHETIC EXAMPLE 1 (DIVERGENT SYNTHESIS)

In a four-necked flask fitted with a nitrogen inlet tube, a thermometer, a cooling tube, and a stirrer was placed 54.6 g of 5-hydroxyisophthalic acid, then 100 g of dimethylformamide (hereinafter abbreviated to DMF) and 35.7 g of pyridine were added to dissolve the 5-hydroxyisophthalic acid. To the resulting solution was added dropwise a solution of 26.5 g of the core component trimesoyl chloride in 50 g of DMF through a dropping funnel over a period of about 30 minutes while maintaining the reaction temperature at 30° C. under a nitrogen atmosphere. The reaction was continued at 30° C. after completion of the dropwise addition and terminated when the absence of trimesoyl chloride in the reaction product was confirmed by GPC analysis.

After completion of the reaction, the residual pyridine was removed under reduced pressure, 200 g of thionyl chloride was added, the mixture was refluxed at 100° C. for 8 hours, and the excess thionyl chloride was distilled off to give 240 g of a solution (38% by weight) of the ester 1 containing terminal acid chloride groups (step 1).

With the use of 120 g of the solution (38% by weight) of the ester 1 obtained in the step 1 as core component in place of trimesoyl chloride used in the preparation of the ester 1 in the aforementioned step 1, the reaction was carried out in the same manner as in the step 1 to give 280 g of a solution (39% by weight) of the second-generation ester 2 containing terminal acid chloride groups (step 2).

Further, with the use of 142 g of the solution (39% by weight) of the ester 2 obtained in the aforementioned step 2 as core component in place of trimesoyl chloride used in the aforementioned step 1, the reaction was carried out in the same manner as in the step 1 to give 308 g of a solution (39% by weight) of the ester 3 containing terminal acid chloride groups (step 3).

In a four-necked flask fitted with a nitrogen inlet tube, a thermometer, a cooling tube, and a stirrer was placed 180 g of pentaerythritol triacrylate as hydroxyl-containing acrylate, 100 g of DMF and 71 g of pyridine were added to dissolve the triacrylate homogeneously, 308 g of the solution (39% by weight) of the ester 3 containing acid chloride groups obtained in the aforementioned step 3 was added dropwise through a dropping funnel over a period of about 30 minutes, and the reaction was continued at 30° C. after completion of the dropwise addition and terminated when the absence of the ester 3 containing acid chloride groups in the reaction product was confirmed by GPC analysis.

The reaction mixture was distilled under reduced pressure to remove the DMF and pyridine to give 250 g of aromatic ester acrylate dendrimer A (third generation) in yellowish white powder as reaction product.

Figure 1:
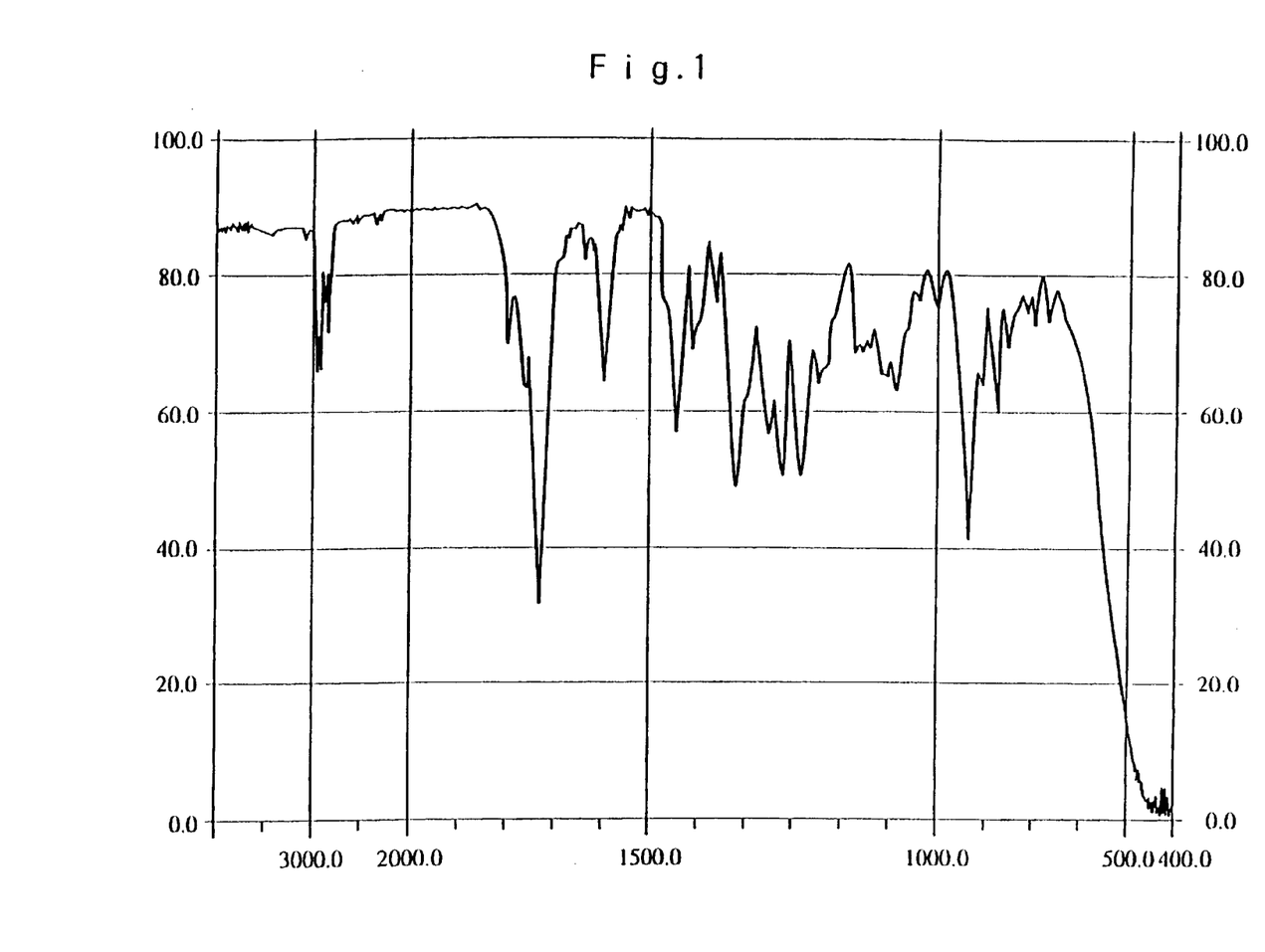
FIG. 1 is the infrared absorption spectrum of the aromatic ester acrylate dendrimer A prepared in Synthetic Example 1.

The infrared absorption spectrum of the aromatic ester acrylate dendrimer A is shown in FIG. 1.

SYNTHETIC EXAMPLE 2 (DIVERGENT SYNTHESIS)

The reaction was carried out as in the aforementioned Synthetic Example 1 except using triglycerol diacrylate as hydroxyl-containing acrylate to give 210 g of aromatic ester acrylate dendrimer B (third generation) in yellowish white powder as reaction product.

SYNTHETIC EXAMPLE 3 (DIVERGENT SYNTHESIS)

The reaction was carried out as in Synthetic Example 1 except using 2-hydroxyethyl acrylate as hydroxyl-containing acrylate to give 180 g of aromatic ester acrylate dendrimer C (third generation) in yellowish white powder as reaction product.

SYNTHETIC EXAMPLE 4 (DIVERGENT SYNTHESIS)

The reaction was carried out as in Synthetic Example 1 except using the acid chloride of mellitic acid containing six acid chloride groups as core component to give 640 g of aromatic ester acrylate dendrimer D (third generation) with melting point 110° C. in yellowish white powder as reaction product.

SYNTHETIC EXAMPLE 5 (DIVERGENT SYNTHESIS)

The reaction was carried out as in Synthetic Example 4 except using triglyerol diacrylate as hydroxyl-containing acrylate to give 590 g of aromatic ester acrylate dendrimer E (third generation) with melting point 110 ° C. in yellowish white powder as reaction product.

SYNTHETIC EXAMPLE 6 (DIVERGENT SYNTHESIS)

The reaction was carried out as in Synthetic Example 4 except using 2-hydroxyethyl acrylate as hydroxyl-containing acrylate to give 490 g of aromatic ester acrylate dendrimer F (third generation) with melting point 110° C. in yellowish white powder as reaction product.

SYNTHETIC EXAMPLE 7 (DIVERGENT SYNTHESIS)

In a four-necked flask fitted with a nitrogen inlet tube, a thermometer, a cooling tube, and a stirrer was placed 54.6 g of 5-hydroxyisophthalic acid, 100 g of DMF and 35.7 g of pyridine were added to dissolve the acid. After dissolution of the acid, 156 g of the solution (39% by weight) of the ester 3 was added dropwise through a dropping funnel over a period of about 30 minutes while maintaining the reaction temperature at 30° C. under a nitrogen atmosphere, and the reaction was continued at 30° C. after completion of the dropwise addition and terminated when the absence of the ester 3 in the reaction product was confirmed by GPC analysis.

After completion of the reaction, the residual pyridine was removed under reduced pressure, 100 g of thionyl chloride was added, the mixture was refluxed at 100° C. for 8 hours, and the excess thionyl chloride was distilled off to give 330 g of a solution (39% by weight) of the ester 4 containing terminal acid chloride groups (step 4).

With the use of 165 g of the solution (39% by weight) of the ester 4 obtained in this step 4, the reaction was carried out in the same manner as in the step 1 to give 330 g of a solution (39% by weight) of the ester 5 containing terminal acid chloride groups (step 5).

Further, with the use of 165 g of the solution (39% by weight) of the ester 5 obtained in this step 5, the reaction was carried out in the same manner as in the step 1 to give 320 g of a solution (39% by weight) of the ester 6 containing terminal acid chloride groups (step 6).

In a four-necked flask fitted with a nitrogen inlet tube, a thermometer, a cooling tube, and a stirrer was placed 144 g of pentaerythritol triacrylate as hydroxyl-containing acrylate, 100 g of DMF and 56.8 g of pyridine were added to dissolve the triacrylate homogeneously, 32 g of the solution (39% by weight) of the ester 6 containing acid chloride groups was added dropwise through a dropping funnel over a period of about 30 minutes, and the reaction was continued at 30 ° C. after completion of the dropwise addition and terminated when the absence of the ester 6 containing terminal acid chloride groups in the reaction product was confirmed by GPC analysis.

The reaction mixture was distilled under reduced pressure to remove the DMF and pyridine to give 150 g of aromatic ester acrylate dendrimer G (sixth generation) in yellowish white powder as reaction product.

SYNTHETIC EXAMPLE 8 (DIVERGENT SYNTHESIS)

The reaction was carried out as in Synthetic Example 6 except using triglycerol diacrylate as hydroxyl-containing acrylate to give 120 g of aromatic ester acrylate dendrimer H (sixth generation) in yellowish white powder as reaction product.

SYNTHETIC EXAMPLE 9 (DIVERGENT SYNTHESIS)

The reaction was carried out as in Synthetic Example 6 except using 2-hydroxyethyl acrylate as hydroxyl-containing acrylate to give 108 g of aromatic ester acrylate dendrimer I (sixth generation) in yellowish white powder as reaction product.

SYNTHETIC EXAMPLE 10 (DIVERGENT SYNTHESIS)

Figure 2:
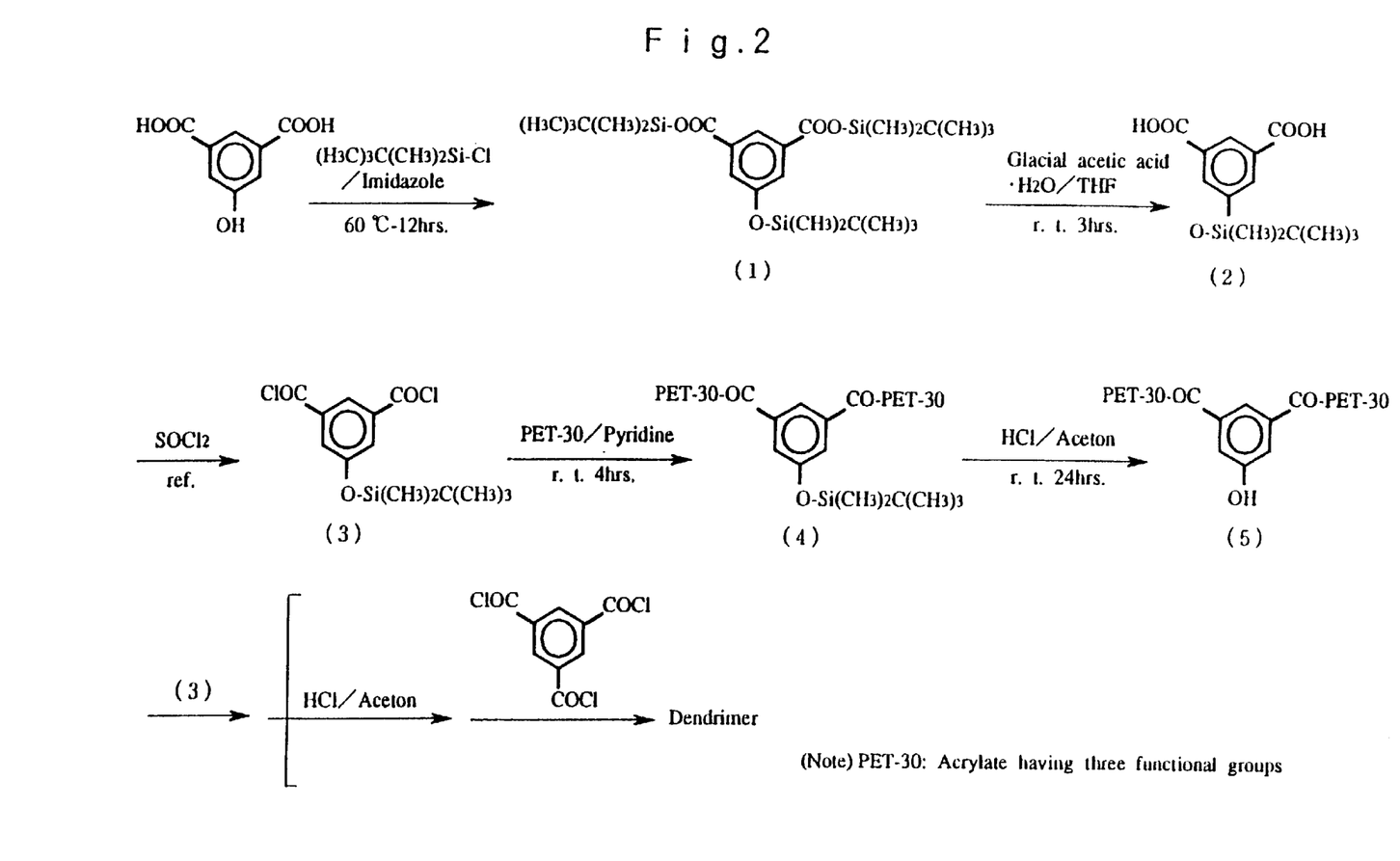
FIG. 2 is a chart illustrating the synthetic route of the aromatic ester acrylate dendrimer by the convergent approach used in Synthetic Example 10.

The synthesis of aromatic ester acrylate dendrimers was conducted as follows in accordance with the synthetic route shown in FIG. 2.

In a four-necked flask fitted with a nitrogen inlet tube, a thermometer, a cooling tube, and a stirrer was placed 18.2 g of 5-hydroxyisophthalic acid, 300 g of DMF and 10.2 g of imidazole were added to dissolve the acid, 30 g of a DMF solution (50% by weight) of 15.7 g of t-butyldimethylchlorosilane as protective group for hydroxyl and carboxyl groups was added dropwise through a dropping funnel over a period of about 30 minutes while keeping the reaction temperature at 30° C. under a nitrogen atmosphere, the temperature was raised to 60° C. after completion of the drowpise addition, the reaction was allowed to proceed for about 12 hours, the reaction mixture was cooled to room temperature, mixed with water, and extracted with hexane three times, and the hexane layer was concentrated to give concentrate (1).

To the concentrate (1) thus obtained were added 628 g of glacial acetic acid, 209 g of water, and 209 g of tetrahydrofuran (hereinafter abbreviated to THF), and the mixture was stirred at room temperature for about 3 hours, filtered, and dried to give 29 g of white solid (2).

In a four-necked flask fitted with a nitrogen inlet tube, a thermometer, a cooling tube, and a stirrer was placed 29 g of the white solid (2), thionyl chloride was added, the mixture was refluxed at 100° C. for 8 hours, and the excess thionyl chloride was distilled off to give 36.5 g of 5-tert-butyldimethylsiloxyisophthalic acid dichloride (3).

In a four-necked flask fitted with a nitrogen inlet tube, a thermometer, a cooling tube, and a stirrer was placed 60 g of pentaerythritol triacrylate (PET-30), 100 g of THF and 20.4 g of pyridine were added to dissolve the triacrylate, 70 g of a THF solution of 36.5 g of 5-tert-butyldimethylsiloxyisophthalic acid dichloride (3) was added dropwise through a dropping funnel over a period of about 30 minutes while keeping the reaction temperature at 30° C. under a nitrogen atmosphere, the reaction was allowed to proceed for about 4 hours, and the THF and pyridine were distilled off under reduced pressure to give 88 g of ester acrylate 7 (4).

In a four-necked flask were placed 88 g of the ester acrylate 7 (4) obtained above, 250 g of 1.0N hydrochloric acid, and 2.2 kg of acetone, the mixture was stirred at 50° C. for about 20 hours and then concentrated, 100 g of THF and 20.4 g of pyridine were added to dissolve the mixture, 18.3 g of a THF solution of 18.3 g of 5-tert-butyldimethylsiloxyisophthalic acid dichloride (3) was added dropwise through a dropping funnel over a period of about 30 minutes while keeping the reaction temperature at 30° C. under a nitrogen atmosphere, and the reaction was allowed to proceed for about 4 hours. The THF and pyridine were distilled off under reduced pressure to give 90 g of ester acrylate 8 (5).

The reaction was repeated in the same manner as above while using the ester acrylate (8) in place of pentaerythritol triacrylate (PET-30) to give 100 g of ester acrylate 9.

Further, 100 g of the ester acrylate (9), 100 g of THF, and 6.8 g of pyridine were placed in a four-necked flask, to the resulting solution was added dropwise 5 g of trimesoyl chloride as core component through a dropping funnel over a period of about 30 minutes while keeping the reaction temperature at 30° C. under a nitrogen atmosphere, the reaction was allowed to proceed at 30° C. for about 6 hours, and the reaction mixture was concentrated and dried under reduced pressure to give 100 g of aromatic ester acrylate dendrimer J.

SYNTHETIC EXAMPLE 11 (DIVERGENT SYNTHESIS)

The reaction was carried out in the same manner as in Synthetic Example 10 except using triglycerol diacrylate as hydroxyl-containing acrylate to give 90 g of aromatic ester acrylate dendrimer K in yellowish white power as reaction product.

SYNTHETIC EXAMPLE 12 (DIVERGENT SYNTHESIS)

The reaction was carried out in the same manner as in Synthetic Example 10 except using 2-hydroxyethyl acrylate as hydroxyl-containing acrylate to give 80 g of aromatic ester acrylate dendrimer L in yellowish white power as reaction product.

Preparation of Curable Resin Compositions

EXAMPLES 1 to 12

Curable resin compositions relating to Examples 1 to 12 were formulated from 50 g each of aromatic ester acrylate dendrimers A to L obtained in the aforementioned Synthetic Examples 1 to 12, 30 g of dipentaerythritol hexaacrylate (hereinafter abbreviated to DPHA), 20 g of tetrahydrofurfuryl acrylate (hereinafter abbreviated to THF-A), and 5 g of a polymerization initiator (Irgacure 1700, product of Ciba-Geigy).

COMPARATIVE EXAMPLE 1

A curable resin composition was formulated for Comparative Example 1 from 60 g of DPHA, the same acrylate as in Example 1, 40 g of THF-A, and 5 g of a polymerization initiator, the same as in Example 1, without the use of aromatic ester acrylate dendrimer.

COMPARATIVE EXAMPLES 2 and 3

Curable resin compositions for Comparative Examples 2 and 3 were formulated as in the aforementioned examples except using 50 g of polycondensation product of bisphenol A type epoxy acrylate and terephthalic acid (molecular weight approximately 3,000; ester acrylate M) or similar polycondensation product (molecular weight approximately 6,000; ester acrylate N) in place of aromatic ester acrylate dendrimer.

The solution viscosity was measured for each of the curable resin compositions thus prepared for Examples 1 to 12 and Comparative Examples 1 to 3 with the aid of a vibrational viscometer.

Then, the performance of all the curable resin compositions of Examples 1 to 12 and Comparative Examples 1 to 3 was assessed as follows.

A chromate-treated and electro-zinc-plated steel plate (0.5 mm thick) and a polycarbonate plate (0.5 mm thick) were used as substrates for each composition. The composition was applied to the substrate by a bar coater to the thickness of 15 $\mu$m, heated at 80 °C. for 1 minute, and UV-cured by irradiation with a high-pressure mercury vapor lamp to prepare a specimen for assessment.

All the specimens were tested for pencil hardness and for adhesion, both initial and at high temperature and humidity as follows.
(1) Pencil Hardness Test Pencil hardness was tested in accordance with JIS-K 5400 with the use of Mitsubishi Uni, the pencil for hardness testing.
(2) Adhesion-crosshatch peeling test Adhesion was tested in accordance with JIS-K 5400 and assessed initially, after heating the specimen at 200° C. for 10 hours, and after keeping the specimen at 70° C. and 90% relative humidity for 500 hours.

As is apparent from the results indicated in Table 1, in comparison with the resin compositions of Comparative Examples 1 to 3 which form films of poor adhesion, particularly at high temperature and humidity, the resin compositions of this invention in Examples 1 to 12, for all their low viscosity, form films of high pencil hardness and good adhesion at high temperature and humidity.

Industrial Applicability

Aromatic ester (meth)acrylate dendrimers of this invention are structurally capable of forming many crosslinking points and curing with high surface hardness and excellent heat and moisture resistance in spite of their low viscosity compared with that of ester acrylates of the same molecular weight and they are useful for components in a variety of curable resin compositions.

Curable resin compositions of this invention contain the aforementioned aromatic ester (meth)acrylate dendrimers of highly branched structure as essential component and they can form coating films of high surface hardness and excellent heat and moisture resistance for all their low viscosity: hence they are potentially applicable as solventless coatings and useful for coatings in the field of electronic materials and metallic materials where long-term reliability is required.

What is claimed is:

1. An aromatic ester (meth)acrylate dendrimer represented by the following general formula (1)

TABLE 1

| | Resin composition | | | | | | | | |
|---|---|---|---|---|---|---|---|---|---|
| | | Solution | PC plate *2 | | | | Zinc-plated steel plate *3 | | |
| | Kind of | viscosity | Adhesion (x/100) | | | | Adhesion (x/100) | | |
| | resin used *1 | at 25° C. (cps) | Initial | High Temperature | High humidity | Pencil hardness | Initial | High Temperature | High humidity | Pencil hardness |

| | Kind of resin | viscosity (cps) | Initial | High Temp | High humidity | Pencil hardness | Initial | High Temp | High humidity | Pencil hardness |
|---|---|---|---|---|---|---|---|---|---|---|
| Example | | | | | | | | | | |
| 1 | A | 11,000 | 100 | 100 | 100 | 3H | 100 | 100 | 100 | 6H |
| 2 | B | 9,500 | 100 | 100 | 100 | 3H | 100 | 100 | 100 | 6H |
| 3 | C | 8,000 | 100 | 100 | 100 | 2H | 100 | 100 | 100 | 5H |
| 4 | D | 17,000 | 100 | 100 | 100 | 4H | 100 | 100 | 100 | 6H |
| 5 | E | 15,000 | 100 | 100 | 100 | 3H | 100 | 100 | 100 | 6H |
| 6 | F | 14,000 | 100 | 100 | 100 | 3H | 100 | 100 | 100 | 6H |
| 7 | G | 21,000 | 100 | 100 | 100 | 4H | 100 | 100 | 100 | 7H |
| 8 | H | 18,000 | 100 | 100 | 100 | 4H | 100 | 100 | 100 | 7H |
| 9 | I | 16,000 | 100 | 100 | 100 | 3H | 100 | 100 | 100 | 6H |
| 10 | J | 9,000 | 100 | 100 | 100 | 3H | 100 | 100 | 100 | 6H |
| 11 | K | 8,500 | 100 | 100 | 100 | 3H | 100 | 100 | 100 | 6H |
| 12 | L | 7,500 | 100 | 100 | 100 | 2H | 100 | 100 | 100 | 6H |
| Comparative Example | | | | | | | | | | |
| 1 | —*4 | 4,500 | 70 | 10 | 0 | 3H | 60 | 10 | 10 | 5H |
| 2 | M*5 | 20,000 | 100 | 60 | 50 | H | 70 | 20 | 10 | 4H |
| 3 | N*6 | 40,000 | 100 | 50 | 40 | H | 80 | 30 | 10 | 4H |

(Notes)
*1): A~L: Aromatic ester acrylate dendrimers of Synthetic Examples 1 to 12
*2): PC plate: Polycarbonate plate
*3): Zinc-plated steel plate: Chromate-treated and electro-zinc-plated steel plate
*4): —: Composition of 60 g of DPHA and 40 g of THF-A
*5): M: Acrylate M
*6): N: Acrylate N (1)

2. An aromatic ester (meth)acrylate dendrimer as described in claim 1 wherein Y in the general formula (1) contains 1 to 3 (meth)acrylic groups.

3. A curable resin composition comprising the aromatic ester (meth)acrylate dendrimer described in claim 1 or 2 and a polymerization initiator as essential components.

4. A coating film obtained by applying the curable resin composition described in claim 3 to a substrate.

* * * * *

UNITED STATES PATENT AND TRADEMARK OFFICE
CERTIFICATE OF CORRECTION

PATENT NO.    : 6,255,444 B1
DATED         : July 3, 2001
INVENTOR(S)   : Masatoshi Yuasa; Hironobu Kawasato; Takero Teramoto It is certified that error appears in the above-identified patent and that said Letters Patent is hereby corrected as shown below:

<u>Title page,</u>
Item [22] PCT Filed, please correct date from "Aug. 7, 1998" to -- Aug. 17, 1998 --.

Signed and Sealed this

Twenty-sixth Day of March, 2002

*Attest:*

*Attesting Officer*

JAMES E. ROGAN
*Director of the United States Patent and Trademark Office*